(12) United States Patent
Wright, IV et al.

(10) Patent No.: US 7,384,653 B2
(45) Date of Patent: Jun. 10, 2008

(54) ORAL DOSAGE FORM COMPRISING A THERAPEUTIC AGENT AND AN ADVERSE-EFFECT AGENT

(75) Inventors: Curtis Wright, IV, Norwalk, CT (US); Anthony E. Carpanzano, Sherman, CT (US)

(73) Assignee: Purdue Pharma L.P., Stamford, CT (US)

( * ) Notice: Subject to any disclaimer, the term of this patent is extended or adjusted under 35 U.S.C. 154(b) by 541 days.

(21) Appl. No.: 10/948,575

(22) Filed: Sep. 23, 2004

(65) Prior Publication Data

US 2005/0063909 A1    Mar. 24, 2005

(51) Int. Cl.
A61K 9/14    (2006.01)
A61K 9/16    (2006.01)
A61K 9/22    (2006.01)
A61K 9/26    (2006.01)
A61K 9/48    (2006.01)

(52) U.S. Cl. .................. 424/489; 424/451; 424/457; 424/458; 424/464; 424/468; 424/469; 424/472; 424/484; 424/490

(58) Field of Classification Search ............... 424/464, 424/465, 468, 469, 470, 471, 472, 474, 489, 424/490, 484
See application file for complete search history.

(56) References Cited

U.S. PATENT DOCUMENTS

| | | |
|---|---|---|
| 2,770,569 A | 11/1956 | Fromherz et al. |
| 3,133,132 A | 5/1964 | Loeb et al. |
| 3,173,876 A | 3/1965 | Zobrist |
| 3,173,877 A | 3/1965 | Jackson et al. |
| 3,276,586 A | 10/1966 | Rosaen |
| 3,332,950 A | 7/1967 | Blumberg et al. |
| 3,493,657 A | 2/1970 | Lewenstein et al. ......... 424/260 |
| 3,541,005 A | 11/1970 | Strathmann et al. |
| 3,541,006 A | 11/1970 | Bixler et al. |
| 3,546,876 A | 12/1970 | Fokker et al. |
| 3,676,557 A | 7/1972 | Lachman et al. |
| 3,773,955 A | 11/1973 | Pachter et al. ............... 424/260 |
| 3,845,770 A | 11/1974 | Theeuwes et al. |
| 3,879,555 A | 4/1975 | Pachter et al. |
| 3,916,889 A | 11/1975 | Russell |
| 3,965,256 A | 6/1976 | Leslie |
| 3,966,940 A | 6/1976 | Pachter et al. ............... 424/260 |
| 3,980,766 A | 9/1976 | Shaw et al. |
| 4,063,064 A | 12/1977 | Saunders |
| 4,088,864 A | 5/1978 | Theeuwes et al. |
| 4,160,020 A | 7/1979 | Ayer et al. |
| 4,176,186 A | 11/1979 | Goldberg |
| 4,200,098 A | 4/1980 | Ayer et al. |
| 4,237,140 A | 12/1980 | Dudzinski |
| 4,285,987 A | 8/1981 | Ayer et al. |
| 4,293,539 A | 10/1981 | Ludwig et al. |
| 4,366,310 A | 12/1982 | Leslie |
| 4,385,057 A | 5/1983 | Bjork et al. |
| 4,401,672 A | 8/1983 | Portoghese et al. |
| 4,424,205 A | 1/1984 | Lahann et al. |
| 4,443,428 A | 4/1984 | Oshlack et al. |
| 4,451,470 A | 5/1984 | Ganti |
| 4,457,933 A | 7/1984 | Gordon et al. ............... 424/260 |
| 4,464,378 A | 8/1984 | Hussain et al. |
| 4,573,995 A | 3/1986 | Chen et al. |
| 4,582,835 A | 4/1986 | Lewis et al. ................. 514/282 |
| 4,587,118 A | 5/1986 | Hsiao |
| 4,608,376 A | 8/1986 | Pasternak |
| 4,661,492 A | 4/1987 | Lewis et al. |
| 4,719,215 A | 1/1988 | Goldberg |
| 4,730,048 A | 3/1988 | Portoghese et al. |
| 4,738,973 A * | 4/1988 | Gittos ........................ 514/328 |
| 4,760,069 A | 7/1988 | Rzeszotarski et al. |
| 4,769,372 A | 9/1988 | Kreek et al. |
| 4,785,000 A | 11/1988 | Kreek et al. |
| 4,798,725 A * | 1/1989 | Patel ........................... 424/456 |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,812,446 A | 3/1989 | Brand |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |

(Continued)

FOREIGN PATENT DOCUMENTS

EP    759303    2/1997

(Continued)

*Primary Examiner*—S. Tran
(74) *Attorney, Agent, or Firm*—Duane Morris LLP

(57) ABSTRACT

The present invention provides an oral dosage form comprising a first composition and a second composition. The first composition comprises an effective amount of a therapeutic agent and the second composition comprises an effective amount of an adverse-effect agent. The adverse-effect agent is covered with a coating that is substantially insoluble in the gastrointestinal tract. In one embodiment, the adverse-effect agent is coated with an outer base-soluble layer and an inner acid-soluble layer. The therapeutic agent can be uncoated or can be coated with a coating having an outer acid-soluble layer and an inner base-soluble layer. The dosage form discourages administration of the therapeutic agent by other than oral administration.

39 Claims, 3 Drawing Sheets

U.S. PATENT DOCUMENTS

| | | |
|---|---|---|
| 4,844,910 A | 7/1989 | Leslie et al. |
| 4,861,598 A | 8/1989 | Oshlack et al. |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlack |
| 4,987,136 A | 1/1991 | Kreek et al. |
| 4,990,341 A | 2/1991 | Goldie et al. |
| 5,026,556 A | 6/1991 | Drust et al. |
| 5,069,909 A | 12/1991 | Sharma et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,199 A | 7/1993 | Hidaka et al. |
| 5,225,440 A | 7/1993 | London et al. |
| 5,226,331 A | 7/1993 | Thompson et al. |
| 5,236,714 A | 8/1993 | Lee et al. |
| 5,240,711 A | 8/1993 | Hille et al. |
| 5,256,669 A | 10/1993 | Askanazi et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,290,816 A | 3/1994 | Blumberg |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,376,705 A | 12/1994 | Leys et al. |
| 5,403,868 A | 4/1995 | Reid et al. |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,703,101 A | 12/1997 | Rose et al. |
| 5,762,963 A | 6/1998 | Byas-Smith |
| 5,763,452 A | 6/1998 | Miller et al. |
| 5,767,125 A | 6/1998 | Crain et al. |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,164 A * | 2/1999 | Kuczynski et al. ......... 424/472 |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,891,919 A | 4/1999 | Blum et al. |
| 5,908,848 A | 6/1999 | Miller et al. |
| 5,935,975 A | 8/1999 | Rose et al. ................ 514/343 |
| 5,942,241 A | 8/1999 | Chasin et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,954 A | 10/1999 | Foss |
| 5,998,434 A | 12/1999 | Mitch et al. |
| RE36,547 E | 2/2000 | Crain et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,143,322 A | 11/2000 | Sackler et al. |
| 6,143,328 A | 11/2000 | Heafield et al. |
| 6,162,467 A | 12/2000 | Miller et al. |
| 6,210,714 B1 | 4/2001 | Oshlack et al. |
| 6,228,398 B1 * | 5/2001 | Devane et al. ............. 424/484 |
| 6,228,863 B1 * | 5/2001 | Palermo et al. ............. 514/282 |
| 6,254,887 B1 | 7/2001 | Miller et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,326,027 B1 | 12/2001 | Miller et al. |
| 6,335,033 B2 | 1/2002 | Oshlack et al. |
| 6,368,629 B1 | 4/2002 | Watanabe et al. |
| 6,375,957 B1 | 4/2002 | Kaiko et al. |
| 6,387,404 B2 | 5/2002 | Oshlack et al. |
| 6,399,096 B1 | 6/2002 | Miller et al. |

| | | | | | |
|---|---|---|---|---|---|
| 6,475,494 B2 | 11/2002 | Kaiko et al. | 2003/0026838 A1 | 2/2003 | Farrell |
| 6,506,407 B2 | 1/2003 | Watanabe et al. | 2003/0059471 A1 | 3/2003 | Compton et al. |
| 6,582,484 B2 | 6/2003 | Wilson | 2003/0064122 A1 | 4/2003 | Goldberg et al. |
| 6,627,635 B2 | 9/2003 | Palermo et al. | 2004/0228802 A1 | 11/2004 | Chang et al. |
| 6,696,066 B2 | 2/2004 | Kaiko et al. | 2005/0163717 A1 | 7/2005 | Anderson et al. |
| 6,696,088 B2 | 2/2004 | Oshlack et al. | 2005/0214223 A1 | 9/2005 | Bartholomaeus et al. |
| 6,716,449 B2 | 4/2004 | Oshlack et al. | 2007/0014732 A1 | 1/2007 | Sackler |
| 6,902,742 B2 | 6/2005 | Devane et al. | | | |
| 7,141,250 B2 | 11/2006 | Oshlack et al. | | | |

FOREIGN PATENT DOCUMENTS

| | | |
|---|---|---|
| 7,144,587 B2 | 12/2006 | Oshlack et al. |
| 7,172,767 B2 | 2/2007 | Kaiko et al. |
| 7,201,920 B2 | 4/2007 | Kumar et al. |
| 2003/0004177 A1 * | 1/2003 | Kao et al. .................. 514/282 |

| | | |
|---|---|---|
| EP | 0759303 A1 * | 2/1997 |
| WO | 00/44353 | 8/2000 |

* cited by examiner

ORAL DOSAGE FORM COMPRISING A THERAPEUTIC AGENT AND AN ADVERSE-EFFECT AGENT

This application claims the benefit of U.S. Provisional Application No. 60/309,791, filed Aug. 6, 2001, the disclosure of which is incorporated by reference herein in its entirety.

1. FIELD OF THE INVENTION

This invention relates generally to an oral dosage form comprising a therapeutic agent and an adverse-effect agent.

2. BACKGROUND OF THE INVENTION

Many therapeutic agents are highly effective for improving quality of life but, because of their abuse potential, may attract drug abusers. For example, opioids are excellent analgesic agents that can control severe and/or chronic pain, such as cancer pain and post-operative pain, but are also subject to abuse by drug users.

Opioids, also known as opioid agonists, are a group of drugs that exhibit opium- or morphine-like properties. Opioids are employed primarily as moderate to strong analgesic agents, but provide other pharmacological effects as well.

There have been previous attempts in the art to control the potential for abuse of opioid analgesics. For example, sustained release forms enable an active ingredient to work over many hours, and such slow release tends to deter illicit use of opioids because abusers tend to prefer the quick euphoric rush, also known as the "burst," provided by immediate release opioids. Drug abusers, however, can defeat the controlled release design by crushing or dissolving the original drug form, for example a tablet, giving them access to snortable and/or injectable opioids that provide the burst. Accordingly, there is an important need for more effective methods of deterring opioid abuse while still keeping orally administered opioids available to patients who have a legitimate need for them.

Prior art approaches to this problem have involved combining an opioid with an opioid antagonist. When administered orally, these combinations provide the pharmacologic action of the opioid with minimal action of the antagonist. When administered parenterally, however, the antagonist can be profoundly antagonistic to the opioid. Particular examples of such combinations include compositions comprising naloxone and morphine or oxymorphone (U.S. Pat. No. 3,493,657 to Lewenstein et al.); methadone and naloxone (U.S. Pat. No. 3,773,955 to Pachter et al.); methadol or acetyl methadol and naloxone (U.S. Pat. No. 3,966,940 to Pachter et al.); oxycodone and naloxone (U.S. Pat. No. 4,457,933 to Gordon et al.); and buprenorphine and naloxone (U.S. Pat. No. 4,582,835 to Lewis et al.). Also, the combination of pentazocine hydrochloride and naloxone has been marketed in the United States as TALWIN NX (Sanofi-Winthrop); VALORON N, a combination of tilidine and naloxone, has been available in Germany for the management of severe pain since 1978; and TEMGESIC NX, a combination of buprenorphine and naloxone, has been available in New Zealand since 1991.

U.S. Pat. No. 6,228,863 to Palermo et al. discloses an oral dosage form of an opioid agonist and an opioid antagonist that reduces the abuse potential of the opioid by combining the agonist and antagonist such that at least two steps are required to separate them.

U.S. Pat. No. 5,935,975 to Rose et al. discloses a method for treating drug dependency by the combined administration of the drug or an agonist of the drug and an antagonist of the drug.

There remains, however, a clear need in the art for more advanced oral dosage forms that are effective for preventing abuse and useful for delivering a therapeutic agent.

3. SUMMARY OF THE INVENTION

The present invention relates to an oral dosage form comprising a first composition and a second composition, wherein the first composition comprises a therapeutic agent and the second composition comprises an adverse-effect agent, wherein the second composition is coated with an inner acid-soluble layer and an outer base-soluble layer.

The invention further relates to an oral dosage form comprising a first composition and a second composition, wherein the first composition comprises a therapeutic agent and is coated with an inner base-soluble layer and an outer acid-soluble layer and the second composition comprises an adverse-effect agent and is coated with an inner acid-soluble layer and an outer base-soluble layer.

The invention further relates to a method for treating or preventing pain, comprising administering to a patient in need thereof the oral dosage form of the invention. In one embodiment the method comprises administering to a patient in need thereof an oral dosage form comprising a first composition and a second composition, wherein the first composition comprises an effective amount of a therapeutic agent; the second composition comprises an effective amount of an adverse-effect agent; an effective amount of the therapeutic agent is released in the patient's small intestine; and less than an effective amount of the adverse-effect agent is released in the patient's gastrointestinal tract.

The invention still further relates to a method for preparing an oral dosage form comprising a first composition and a second composition, wherein the first composition comprises a therapeutic agent and the second composition comprises an adverse-effect agent, wherein the second composition is coated with an inner acid-soluble layer and an outer base-soluble layer, the method comprising the step of preparing the oral dosage form as set forth herein.

The invention still further relates to a method for preparing an oral dosage form comprising a first composition and a second composition, wherein the first composition comprises a therapeutic agent and is coated with an inner base-soluble layer and an outer acid-soluble layer and the second composition comprises an adverse-effect agent and is coated with an inner acid-soluble layer and an outer base-soluble layer, the method comprising the step of preparing the oral dosage form as set forth herein.

4. BRIEF DESCRIPTION OF THE DRAWINGS

5. DETAILED DESCRIPTION OF THE INVENTION

Figures 1, 2:
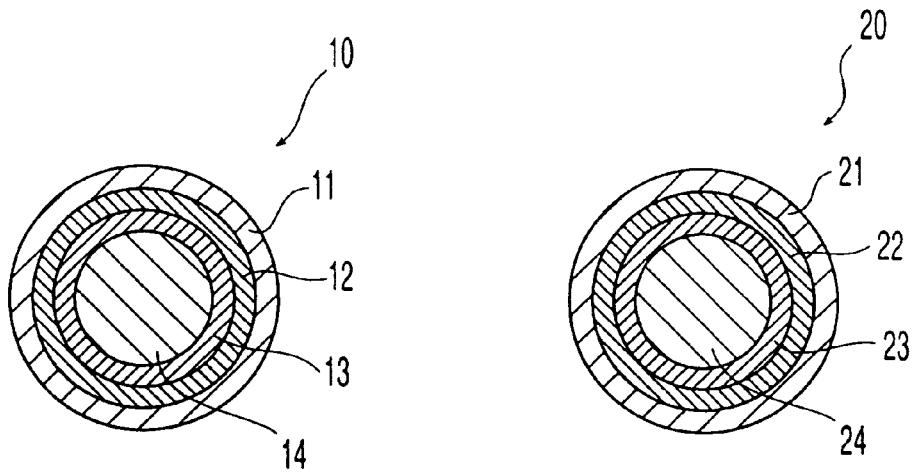
FIG. 1 shows a cross-sectional view of a coated granule of a first composition useful in the oral dosage forms of the invention.
FIG. 2 shows a cross-sectional view of a coated granule of a second composition useful in the oral dosage forms of the invention.

The oral dosage form of the present invention comprises a first composition and a second composition. The first composition comprises a therapeutic agent, and the second composition comprises an adverse-effect agent.

The term "therapeutic agent," as used herein, means any drug intended to have a beneficial effect when administered to a patient.

The term "adverse-effect agent," as used herein, means an agent that (A) reduces or eliminates one or more pharmacological effects of the therapeutic agent, such as a euphoric or toxic effect or (B) causes an undesired physiological reaction, such as emesis.

In a first embodiment of the oral dosage form of the invention, the second composition is coated with a layer that is substantially insoluble in the gastrointestinal tract. Thus, when the oral dosage form of the present invention is orally administered to a patient as intended, only the therapeutic agent is released in the gastrointestinal tract of the patient, and the adverse-effect agent is not released. If the oral dosage form is tampered with so that the coating on the second composition is damaged, however, then not only the therapeutic agent but also the adverse-effect agent are released upon administration.

In a second embodiment the second composition is coated with an outer base-soluble layer and an inner acid-soluble layer, which is not dissolved when orally administered to a patient.

In a third embodiment of the oral dosage form of the invention, both the first composition and second composition have a coating comprising at least two layers, an acid-soluble layer and a base-soluble layer, but the order of the layers in the coating on the first composition is different from that of the layers in the coating on the second composition. The coating covering the first composition comprises an outer acid-soluble layer and an inner base-soluble layer, which are dissolved when orally administered to a patient. On the other hand, the coating covering the second composition comprises an outer base-soluble layer, which gets dissolved when orally administered, and an inner acid-soluble layer, which does not get dissolved when orally administered to a patient.

When orally administered to a patient, the oral dosage form passes through the stomach first, where its acidic environment dissolves the first composition's outer acid-soluble layer, and then passes into the small intestine, where its basic environment dissolves the first composition's inner base-soluble layer. Here, the therapeutic agent can be absorbed by the body. In contrast, the second composition is coated with an outer base-soluble layer, which is substantially insoluble in the stomach's acidic environment. Therefore, the second composition passes through the stomach with both the outer base-soluble layer and the inner acid-soluble layer intact. When the second composition enters the small intestine, the outer base-soluble layer dissolves, exposing the inner acid-soluble layer, which is substantially insoluble in the small intestine's basic environment, so that the adverse-effect agent cannot be absorbed by the body. Thus, when the oral dosage form of the present invention is orally administered to a patient, for example a human, as intended, only the therapeutic agent is released in the gastrointestinal tract and absorbed by the patient; the adverse-effect agent is not released and, therefore, not available for absorption into the body. Here, the therapeutic agent works as if it were administered alone without the adverse-effect agent, since only the therapeutic agent is available for absorption by the body.

However, if the oral dosage form of the present invention is tampered with, e.g., chewed, crushed, ground or dissolved, particularly in a solvent with heat (e.g., greater than about 45° C. to about 50° C.), then not only the therapeutic agent but also the adverse-effect agent becomes available for absorption into the body. The adverse-effect agent can then exert its effect by either reducing the effect of the therapeutic agent or eliciting an unpleasant effect in the patient. Thus, where the adverse-effect agent is an antagonist of the therapeutic agent, the effects of the therapeutic agent are drastically diminished or even eliminated by the effects of the adverse-effect agent. For example, where the therapeutic agent is an opioid agonist and the adverse-effect agent is an opioid antagonist, and the oral dosage form is tampered with, the opioid antagonist becomes bioavailable, interfering with opioid-receptor binding and reducing the opioid antagonist's pharmacological effects. Accordingly, only patients who take the dosage form of the present invention as intended, i.e, orally as an intact dosage form, can experience the full pharmacological effects of the therapeutic agent. Where the adverse-effect agent is an emetic agent and the oral dosage form is tampered with, the emetic agent induces vomiting which discourages the user from tampering with the dosage form. Moreover, where the adverse-effect agent causes vomiting the oral dosage form of the invention not only discourages users from tampering with it, but can also be effective to remove the therapeutic agent from subject's body. Abusing the therapeutic agent becomes less desirable when present in the oral dosage form of the present invention because, when tampered with, the adverse-effect agent exerts its undesirable effects.

In one embodiment of the present invention, the first composition is intended to be released slowly after it is orally administered to the subject. This prevents the burst, which some abusers seek. The first composition can be formulated as a slow release formulation, for example, by further coating the first composition with a sustained-release coating that slowly dissolves so that all the therapeutic agent is not released at once. In the embodiments where the first composition is coated with an outer acid-soluble layer and an inner base-soluble layer, the sustained-release coating is an innermost layer. In another embodiment the first composition can be formulated as a slow release formulation by incorporating the therapeutic agent into a matrix that slowly releases the therapeutic agent over time. Therapeutic agents intended to be released slowly, when orally administered to a subject, may have side effects if released all at once, rather than slowly. The coated second composition prevents tampering, which would result in immediate release of the therapeutic agent.

FIG. 1 shows a cross-sectional view of an embodiment of the coated first composition 10. A first composition 14 is covered with an innermost sustained-release coating 13 (optional), an inner base-soluble layer 12, and an outer acid-soluble layer 11.

FIG. 2 shows a cross-sectional view of an embodiment of the coated second composition 20. A second composition 24 is covered with an inner acid-soluble layer 23, an outer base-soluble layer 22 and an outermost layer that is substantially insoluble in the gastrointestinal tract 21 (optional).

5.1 Therapeutic Agent

Any kind of therapeutic agent can be used in the oral dosage forms of the present invention. In one embodiment the oral dosage from is used in situations where there is a potential toxicity or overdose associated with the uncontrolled release of the drug due to tampering with the dosage form. Examples of useful therapeutic agents include, but are not limited to, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile-dysfunction-improvement agents, immunosuppressants, anti-protozoal agents, anti-thyroid agents, anxiolytic agents, sedatives, hypnotics, neuroleptics, β-blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, and non-essential fatty acids. The first composition can comprise more than one therapeutic agent.

The phrase "therapeutic agent" is also meant to encompass all pharmaceutically acceptable salts of the therapeutic agent. Pharmaceutically acceptable salts include, but are not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like.

In another embodiment the therapeutic agent has potential for abuse. The abuse potential of a drug is established by many factors, which may include the following: (1) the capacity of the drug to produce the kind of physical dependence in which drug withdrawal causes sufficient distress to bring about drug-seeking behavior; (2) the ability to suppress withdrawal symptoms caused by withdrawal from the drug; and (3) the degree to which the drug induces euphoria similar to that produced by morphine and other opioids. The term "a therapeutic agent having abuse potential," as used herein, refers to a therapeutic agent having at least one of the above-identified factors. Examples of therapeutic agents having abuse potential include, but are not limited to, opioids, benzodiazepines, barbiturates, and stimulants, such as methylphenidate and amphetamines.

The term "opioid" refers to a substance that binds, optionally stereo-specifically, to any of several subspecies of opioid receptors and produces an agonist action. Opioids include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, PANTOPON, papaveretum, paregoric, pentazocine, phenadoxone, phendimetrazine, phendimetrazone, phenomorphan, phenazocine, phenoperidine, piminodine, piritramide, prophepkazine, promedol, properidine, propoxyphene, propylhexedrine, sufentanil, tilidine, tramadol, pharmaceutically acceptable salts thereof, and mixtures thereof.

In certain embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol, pharmaceutically acceptable salts thereof, and mixtures thereof. In one embodiment the opioid agonist is oxycodone or hydrocodone.

The term "benzodiazepines" refers to drugs that are derivatives of benzodiazepine and are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, pharmaceutically acceptable salts thereof, and mixture thereof.

Barbiturates refer to sedative-hypnotic drugs derived from barbituric acid (2,4,6,-trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital, pharmaceutically acceptable salts thereof, and mixtures thereof.

Stimulants refer to drugs that stimulate the central nervous system. Stimulants include, but are not limited to, amphetamines, such as amphetamine, amphetamine, dextroamphetamine resin complex, dextroamphetamine, methamphetamine, methylphenidate, pharmaceutically acceptable salts thereof and mixtures thereof.

Other examples of therapeutic agent having potential for abuse include, but are not limited to, dronabinol, glutethimide, methylphenidate, nabilone, anabolic steroids, methylprylon, ethchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, and detropropoxyphene.

The therapeutic agent may also be an agent intended for delivery to the colon. Therapeutic agents intended for delivery to the colon include, but are not limited to, agents that act locally in the colonic region to treat a colon diseases such as irritable bowel syndrome, irritable bowel disease, Crohns disease, constipation, post operative atony, gastrointestinal infections, and therapeutic agents that deliver antigenic material to the lymphoid tissue. Agents for the treatment of colon disease, include, but are not limited to 5-ASA; steroids, such as hydrocortisone and budesonide; laxatives; octreotide; cisapride; anticholinergics; opioids; calcium channel blockers; DNA for delivery to the cells of the colon; glucosamine; thromboxane $A_2$ synthetase inhibitors, such as Ridogrel; 5HT3-antagonists, such as ondansetron; antibodies against infectious bacteria, such as *Clostridium difficile*; and antiviral agents, for example, for the prophylaxis of HIV.

Alternatively, the therapeutic agent can be an agent that is systemically active and for which absorption is improved in the colon region. Such drugs include polar compounds such as: heparins; insulin; calcitonins; human growth hormone (HGH); growth hormone releasing hormone (GHRH); interferons; somatostatin and analogues such as octreotide and vapreotide; erythropoietin (EPO); granulocyte colony stimulating factor (GCSF); parathyroid hormone (PTH); luteinising hormone releasing hormone (LHRH) and analogues thereof; atrial natriuretic factor (ANF); vasopressin; desmopressin; calcitonin gene related peptide (CGRP); and analgesics.

5.2 Adverse-Effect Agent

The adverse-effect agent can be an agent that reduces or eliminates the therapeutic agent's pharmacological activities including, but not limited to: (1) the capacity of the drug to produce the kind of physical dependence in which drug withdrawal causes sufficient distress to bring about drug-seeking behavior; (2) the ability to suppress withdrawal symptoms caused by withdrawal from the drug; and (3) the induction of euphoria similar to that produced by morphine and other opioids. Adverse-effect agents that reduce or eliminate the pharmacological effects of the therapeutic agent include, but are not limited to, antagonists of the therapeutic agent agonist. When an opioid agonist is used as the therapeutic agent in the oral dosage form of the present invention, an opioid antagonist can be used as the adverse-effect agent. Likewise, when a benzodiazepine is used as the therapeutic agent in the oral dosage form of the present invention, a benzodiazepine antagonist can be used as the adverse-effect agent. When a barbiturate is used as a therapeutic agent in the oral dosage form of the present invention, a barbiturate antagonist can be used as the adverse-effect agent. When an amphetamine is used as a therapeutic agent in the oral dosage form of the present invention, an amphetamine antagonist can be used as the adverse-effect agent. When the therapeutic agent is toxic when dosed above its normal therapeutic range, i.e., there is a potential for an overdose, then an antidote of the toxic therapeutic agent can be used as the adverse-effect agent.

The phrase "adverse-effect agent" is also meant to encompass all pharmaceutically acceptable salts of the adverse-effect agent. Pharmaceutically acceptable salts include, but are not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like.

Opioid antagonists that can be used as the adverse-effect agent of the present invention include, but are not limited to, naloxone, naltrexone, nalmefene, cyclazacine, levallorphan, and mixtures thereof. In certain embodiments, the opioid antagonist is naloxone or naltrexone.

Benzodiazepine antagonists that can be used as the adverse-effect agent of the present invention include, but are not limited to, flumazenil.

Barbiturate antagonist which can be used as the adverse-effect agent of the present invention include, but are not limited to, amphetamines, described herein.

Stimulant antagonists that can be used as the adverse-effect agent of the present invention include, but are not limited to, benzodiazepines, described herein.

In another embodiment of the present invention, the adverse-effect agent is an agent that causes an undesired physiological reaction, such as emesis. This type of adverse-effect agent can be used with any kind of therapeutic agent including an opioid, a benzodiazepine, a barbiturate, and a stimulant. Examples of emetic agents suitable for use as the adverse-effect agent in the present invention includes any drug that safely and effectively induces vomiting after administration including, but not limited to, ipecac and apomorphine.

5.4 Coatings 5.4.1. Coatings Insoluble in the Gastrointestinal Tract

Examples of useful coatings that are substantially insoluble in the gastrointestinal tract include, but are not limited to, coatings comprising a hydrophobic material. In one embodiment the coating that is substantially insoluble in the gastrointestinal tract comprises a cellulose polymer. In certain embodiments, the cellulose polymer is a cellulose ether, a cellulose ester, or a cellulose ester ether. In one embodiment, the cellulose polymers have a degree of substitution, D.S., on the anhydroglucose unit of from zero up to and including 3. By "degree of substitution" is meant the average number of hydroxyl groups present on the anhydroglucose-unit of the cellulose polymer that are replaced by a substituting group. Representative cellulose polymers include, but are not limited to, polymers selected from cellulose acylate, cellulose diacylate, cellulose triacylate, cellulose acetate, cellulose diacetate, cellulose triacetate, mono, di, and tricellulose alkanylates, mono, di, and tricellulose aroylates, and mono, di, and tricellulose alkenylates. Exemplary cellulose polymers include cellulose acetate having an acetyl content up to about 21%; cellulose acetate having an acetyl content up to about 32 to 39.8%; cellulose acetate having a D.S. of about 1 to 2 and an acetyl content of about 21 to 35%; and cellulose acetate having a D.S. of about 2 to 3 and an acetyl content of about 35 to 44.8%. In one embodiment, the cellulose polymer is ethylcellulose, cellulose acetate, cellulose propionate (low, medium, or high molecular weight), cellulose acetate propionate, cellulose acetate butyrate, cellulose acetate phthalate, or cellulose triacetate. In one embodiment, the ethylcellulose has an ethoxy content of about 44 to 55%.

More specific cellulose polymers include cellulose propionate having a D.S. of about 1.8 and a propyl content of about 39.2 to 45% and a hydroxyl content of about 2.8 to 5.4%; cellulose acetate butyrate having a D.S. of about 1.8, an acetyl content of about 13 to 15%, and a butyryl content of about 34 to 39%; cellulose acetate butyrate having an acetyl content of about 2 to 29%, a butyryl content of about 17 to 53%, and a hydroxyl content of about 0.5 to 4.7%;

cellulose triacylate having a D.S. of about 2.9 to 3 such as cellulose triacetate, cellulose trivalerate, cellulose trilaurate, cellulose tripatmitate, cellulose trisuccinate, and cellulose trioctanoate; cellulose diacylates having a D.S. of about 2.2 to 2.6 such as cellulose disuccinate, cellulose dipalmitate, cellulose dioctanoate, cellulose dipentanoate, and coesters of cellulose such as cellulose acetate butyrate, cellulose acetate octanoate butyrate, and cellulose acetate propionate.

Additional cellulose polymers useful for coating the second composition with a coating that is substantially insoluble in the gastrointestinal tract include, but are not limited to, acetaldehyde dimethyl cellulose acetate, cellulose acetate ethylcarbamate, cellulose acetate methylcarbamate, and cellulose acetate dimethylaminocellulose acetate.

Acrylic polymers are also useful for coating the second composition with a coating that is substantially insoluble in the gastrointestinal tract. Acrylic polymers include, but are not limited to, acrylic resins comprising copolymers synthesized from acrylic and methacrylic acid esters (e.g., the copolymer of acrylic acid lower alkyl ester and methacrylic acid lower alkyl ester) containing about 0.02 to 0.03 moles of a tri (lower alkyl) ammonium group per mole of acrylic and methacrylic monomer. In one embodiment, the acrylic resin is Eudragit RS 30 D manufactured by Röhm Tech Inc. of Fitchburg, Mass. Eudragit RS 30 D is a water insoluble copolymer of ethyl acrylate (EA), methyl methacrylate (MM) and trimethylammonioethyl methacrylate chloride (TAM) in which the molar ratio of TAM to the remaining components (EA and MM) is 1:40. Aqueous suspensions of acrylic resins such as EUDRAGIT RS can be used to coat the adverse-effect agent of the invention.

In certain embodiments of the invention, the acrylic polymer is selected from acrylic acid and methacrylic acid copolymers, methyl methacrylate copolymers, ethoxyethyl methacrylates, cyanoethyl methacrylates, poly(acrylic acid), poly(methacrylic acid), methacrylic acid alkylamide copolymers, poly(methyl methacrylate), polymethacrylate, poly (methyl methacrylate) copolymer, polyacrylamide, aminoalkyl methacrylate copolymer, poly(methacrylic acid anhydride), and glycidyl methacrylate copolymers.

When a cellulose polymer or an acrylic polymer is used as a coating that is substantially insoluble in the gastrointestinal tract, suitable plasticizers, e.g., acetyl triethyl citrate and/or acetyl tributyl citrate, may also be admixed with the polymer. The coating that is substantially insoluble in the gastrointestinal tract may also contain additives such as coloring agents, talc, and/or magnesium stearate, which are well known in the coating art.

Polymers useful for coating the second composition with a coating that is substantially insoluble in the gastrointestinal tract also include, but are not limited to, poly(lactic/glycolic acid) ("PLGA") copolymers, polylactides, polyglycolides, polyanhydrides, polyorthoesters, polycaprolactones, polyphosphazenes, polysaccharides, proteinaceous polymers, polyesters, polydioxanone, polygluconate, polylactic-acid polyethylene oxide copolymers, poly(hydroxybutyrate), polyphosphoesters, and mixtures thereof.

In certain embodiments, the polymer comprises a poly (lactic/glycolic acid) copolymer, a copolymer of lactic and glycolic acid, having a molecular weight of about 2,000 to about 500,000 daltons. The ratio of lactic acid to glycolic acid is from about 100:0 to about 25:75, in one embodiment from about 65:35. Poly(lactic/glycolic acid) may be prepared by the procedure set forth in U.S. Pat. No. 4,293,539 to Ludwig et al., the disclosure of which is expressly incorporated herein by reference thereto.

The coating that is substantially insoluble in the gastrointestinal tract is of sufficient thickness to prevent release of the adverse-effect agent from the second composition while it is in the gastrointestinal tract. Many of the coatings that are substantially insoluble in the gastrointestinal tract are slowly biodegraded or dissolved in an aqueous environment and, after sufficient time, will eventually release the adverse-effect agent. Accordingly, the coating should be of a sufficient thickness that does not permit the adverse effect agent to be released during the time that the adverse-effect agent is present in the gastrointestinal tract. The thickness of the coating will depend on the characteristics of the coating composition being used.

5.4.2 Acid-Soluble Layer

In various embodiments, the coating useful in the present invention comprises an acid-soluble layer. The term "acid-soluble layer" refers to a layer that is substantially soluble at a pH of less than about pH 5.0, but substantially insoluble at a pH of greater than about pH 5.5. In one embodiment, the acid-soluble layer is substantially soluble at a pH of less than about pH 4.0, but substantially insoluble at a pH of greater than about pH 4.5. In another embodiment, the acid-soluble layer is substantially soluble at a pH of less than about pH 3.0, but substantially insoluble at a pH of greater than about pH 3.5. The acid-soluble layer typically comprises an acid-soluble polymer.

As used herein, the phrase "substantially soluble," when used to describe a layer, means soluble to a degree that a portion of that which the layer covers, for example, an acid-soluble layer, a base-soluble layer, a first composition, or a second composition, is made available to the environment of the gastrointestinal tract in an effective amount.

As used herein, the phrase "substantially insoluble," when used to describe a layer, means that the layer does not dissolve or does so only to a degree that a portion of that which the layer covers, for example, an acid-soluble layer, a base-soluble layer, a first composition, or a second composition, is not made available to the environment of the gastrointestinal tract or is made available to the environment of the gastrointestinal tract in less than an effective amount.

In one embodiment, the acid-soluble polymer has a dimethylaminoethyl ammonium functionality. Such a polymer is commercially available as EUDRAGIT E 100 or Eudragit E PO from Rohm Pharma GmbH, Weiterstat, Germany. Examples of other suitable acid-soluble polymers can be found in "Materials Used in Pharmaceutical Formulations," edited by A. T. Florence, Society of Chemical Industries, 1984.

5.4.3 Base-Soluble Layer

In various embodiments, the coating of the present invention comprises a base-soluble layer. The term "base-soluble layer" refers to a layer that is substantially soluble at a pH of greater than about pH 5.5, but substantially insoluble at a pH of less than about 5.0. In one embodiment, the base-soluble layer is substantially soluble at a pH of greater than about pH 6.5, but substantially insoluble at a pH of less than about 6.0. In another embodiment, the base-soluble layer is substantially soluble at a pH of greater than about pH 7.5, but substantially insoluble at a pH of less than about 7.0. The base-soluble layer generally comprises a base-soluble polymer. In one embodiment, the base-soluble polymer is an anionic copolymer of methacrylic acid and methacrylates having carboxylic acid functionalities. Such a polymer is commercially available as EUDRAGIT L 100-55, EUDRAGIT L 30D-55, EUDRAGIT L, or EUDRAGIT S 100 (commercially available from Rohm Pharma GmbH, Weiterstat, Germany). Examples of other suitable base-soluble polymers can be found in "Materials Used in Pharmaceutical Formulations," edited by A. T. Florence, Society of Chemical Industries, 1984.

5.4.4 Slow-Release Formulations

In one embodiment, the therapeutic agent is released slowly over time. Suitable controlled-release formulations known to those of ordinary skill in the art, including those described herein, can be readily selected for use with the oral dosage forms of the invention. Single unit dosage forms suitable for oral administration, such as tablets, capsules, gelcaps, caplets, and the like, that are adapted for controlled-release are encompassed by the present invention.

The controlled release of the therapeutic agent from the first composition can be stimulated by various inducers, for example pH, temperature, enzymes, water, or other physiological conditions or compounds. The controlled release of the therapeutic agent can be achieved, for example by coating or admixing the therapeutic agent with a controlled-release component. The term "controlled-release component" in the context of the present invention is defined herein as a compound or mixture of compounds, including polymers, polymer matrices, gels, permeable membranes, liposomes, microspheres, or the like, or a combination thereof, that facilitates the controlled-release of the therapeutic agent from the first composition of the oral dosage form of the invention.

As discussed above, in one embodiment of the invention the therapeutic agent is formulated for controlled release by coating the therapeutic agent with a sustained-release coating. The term "sustained-release coating" refers to a coating made of one or more materials that allows for the slow release of the drug over time. In one embodiment, the sustained-release coating is a pH-independent layer, i.e., a coating that has a defined permeability that is not influenced by pH. The term "pH-independent layer" means that the difference, at any given time, between the amount of drug released at, e.g., pH 1.6, and the amount released at any other pH, e.g., pH 7.2, when measured using a specific method, such as, for example, the USP Paddle Method at 100 rpm in 900 ml aqueous buffer, is 10% (by weight) or less.

Any sustained-release coating known to those of ordinary skill in the art can be used in the oral dosage form of the invention. Sustained-release coatings are well known in the art (See, e.g., Remingtons Pharmaceutical Sciences, $18^{th}$ ed. Mack Publishing Co., Easton, Pa., 1990, p. 1670). Typically, the sustained-release coating comprises a water-insoluble material, such as a wax or a wax-like substance, fatty alcohol, shellac, zein, hydrogenated vegetable oil, water insoluble cellulose, polymer of acrylic and/or methacrylic acid, or any other slowly digestible or dissolvable solid known in the art. The coating formulations useful in the present invention should be capable of producing a strong, continuous film that is smooth and elegant, capable of supporting pigments and other coating additives, non-toxic, inert, and tack-free. Generally, the film coat is applied to the first composition, for example when in the form of a tablet or a granule, to achieve a weight gain level from about 2 to about 25 percent. However, the film coat may be lesser or greater depending upon the physical properties of the therapeutic agent included in the formulation and the desired release rate.

In one embodiment, the sustained-release coating comprises a hydrophobic polymer. In another embodiment, the hydrophobic polymer comprises a water-insoluble cellulosic polymer, such as an alkylcellulose, for example ethylcellulose; an acrylic polymer; or mixtures thereof.

In another embodiment, the sustained-release coating comprises an acrylic polymer. Any acrylic polymer that is pharmaceutically acceptable can be used. For example, the acrylic polymer can be an acrylate or methacrylate, formed from one or more of acrylic acid, methacrylic acid, acrylic acid esters, and methacrylic acid esters. These polymers can be cationic, anionic, or non-ionic, so that it is possible to obtain polymers that are soluble in, or resistant to dissolution, over a wide range of pH values. Some acrylic polymers useful for the purposes of the present invention are those that are marketed under the trade name EUDRAGIT (commercially available from Rohm Pharma GmbH, Weiterstat, Germany). Examples of suitable acrylic polymers include, but are not limited to, acrylic acid and methacrylic acid copolymers, methyl methacrylate polymers, methyl methacrylate copolymers, ethoxyethyl methacrylates polymers, cyanoethyl methacrylate polymers, aminoalkyl methacrylate copolymers, poly(acrylic acid), poly(methacrylic acid), methacrylic acid alkylamine copolymers, poly(methyl methacrylate), poly(methacrylic acid)(anhydride), polymethacrylate, polyacrylamide, poly(methacrylic acid anhydride), and glycidyl methacrylate copolymers.

The acrylic polymer can comprise one or more ammonio methacrylate copolymers. Ammonio methacrylate copolymers are well known in the art, and are fully polymerized copolymers of acrylic and methacrylic acid esters with a low content of quaternary ammonium groups. In order to obtain a desirable dissolution profile for a given therapeutic agent, it might be necessary to incorporate two or more ammonio methacrylate copolymers having differing physical properties. For example, it is known that by changing the molar ratio of the quaternary ammonium groups to neutral (meth) acrylic esters, the permeability properties of the resultant coating can be modified. One of ordinary skill in the art will readily know how to combine monomers to provide a copolymer that releases the therapeutic agent at the desired release rate. Copolymers of acrylate and methacrylate having a quaternary ammonium group functionality are commercially available as EUDRAGIT RS and EUDRAGIT RL from Rohm Pharma GmbH, Weiterstat, Germany.

Other polymers suitable for use in the invention include, but are not limited to, hydroxyalkylcelluloses; poly(lactic/glycolic acid) ("PLGA"); polylactide; polyglycolide; polyanhydrides; polyorthoesters; polycaprolactone; polyphosphazenes; polysaccharides; proteinaceous polymers; polyesters; polydioxanone; polygluconate; polylactic-acid polyethylene oxide copolymers; poly(hydroxybutyrate) polyphosphoesters; or mixtures thereof.

The inclusion of an effective amount of a plasticizer in the aqueous dispersion of hydrophobic polymer can further improve the physical properties of the film. For example, because ethylcellulose has a relatively high glass-transition temperature ("Tg") and does not form flexible films under normal coating conditions, it is often necessary to plasticize the ethylcellulose before using it as a coating material.

The suitability of a plasticizer may relate to its affinity or solvating power for the polymer and its effectiveness for interfering with polymer-polymer attachments. Such activity imparts a desired flexibility to the polymer by relieving molecular rigidity. An important parameter in determining the suitability of a plasticizer for a polymer is related to the Tg of the polymer. The Tg is related to the temperature or temperature range where there is a fundamental change in the physical properties of the polymer. This change does not reflect a change in state, but rather a change in the macromolecular mobility of the polymer. Below the Tg, polymer chain mobility is severely restricted. Thus, for a given polymer, if the Tg is above room temperature, the polymer will behave as a glass at room temperature, being hard, non-pliable, and rather brittle: properties that are restrictive for a film coating since the coated dosage form may be subjected to a certain amount of external stress. Incorporation of suitable plasticizers into the polymer matrix effectively reduces the Tg, so that under ambient conditions the films are softer, more pliable and often stronger, and, thus, better able to resist mechanical stress. Other aspects of suitable plasticizers include their ability to act as a good "swelling agent," especially for ethylcellulose, and to improve the solubility profile of the coating in water.

Examples of suitable plasticizers for ethylcellulose include dibutyl sebacate, diethyl phthalate, triethyl citrate, and tributyl citrate, although other plasticizers (such as acetylated monoglycerides, phthalate esters and castor oil) can be used. In one embodiment, triethyl citrate is a plasticizer for the aqueous dispersions of ethyl cellulose.

Examples of suitable plasticizers for the acrylic polymers useful in the present invention include, but are not limited to, citric acid esters such as triethyl citrate, tributyl citrate, dibutyl phthalate, and 1,2-propylene glycol. Other plasticizers suitable for enhancing the elasticity of the films formed from acrylic films, such as EUDRAGIT RL/RS lacquer solutions, include polyethylene glycols, propylene glycol, diethyl phthalate, castor oil, and triacetin. The plasticizer is typically added to a solution of the polymer in an aqueous or non-aqueous solvent that is used to coat the first composition.

Generally, the amount of plasticizer included in a coating solution is based on the concentration of the coating. In one embodiment, the amount of plasticizer included in a coating solution of ethylcellulose is from about 1 to about 50 percent by weight of the ethylcellulose. In another embodiment, the amount of plasticizer included in a coating solution of an aqueous dispersion of acrylic polymer is about 20%. The necessary concentration of the plasticizer for a particular coating solution and method of application can be readily determined by one of ordinary skill in the art without undue experimentation.

A commercially available aqueous dispersion of ethylcellulose suitable for use in the invention is AQUACOAT (commercially available from FMC Corp., Philadelphia, Pa., U.S.A.). AQUACOAT is prepared by dissolving ethylcellulose in a water-immiscible organic solvent and then emulsifying the organic solvent in water in the presence of a surfactant and a stabilizer. After homogenization to generate submicron droplets, the organic solvent is evaporated under vacuum to form a pseudolatex. Plasticizer is not incorporated in the pseudolatex during the manufacturing phase; therefore, prior to using the pseudolatex as a coating, it is necessary to intimately mix the AQUACOAT with a suitable plasticizer.

Another commercially available aqueous dispersion of ethylcellulose suitable for use in the invention is SURE-LEASE (commercially available from Colorcon, Inc., West Point, Pa., U.S.A.).

In one embodiment, the acrylic coating comprises an acrylic resin lacquer used in the form of an aqueous dispersion, such as EUDRAGIT. In further embodiments, the acrylic coating comprises a mixture of two acrylic resin lacquers commercially available from Rohm Pharma GmbH, Weiterstat, Germany under the tradenames EUDRAGIT RL 30 D and EUDRAGIT RS 30 D. These materials are copolymers of acrylic and methacrylic esters having a low content of quaternary ammonium groups, the molar ratio of ammonium groups to the remaining neutral (meth)acrylic esters being 1:20 in EUDRAGIT RL 30 D and 1:40 in EUDRAGIT RS 30 D. The mean molecular weight of these materials is about 150,000. The code designations RL (high permeability) and RS (low permeability) refer to the permeability properties of these agents. EUDRAGIT RL/RS mixtures are substantially insoluble in water and in digestive fluids. However, coatings formed from the same are swellable and permeable in aqueous solutions and digestive fluids. The EUDRAGIT RL/RS dispersions useful in the present invention can be mixed together in any desired ratio in order to ultimately obtain a controlled-release formulation having a desirable dissolution profile. Desirable controlled-release formulations can be obtained, for instance, from a coating derived from 100% EUDRAGIT RL; 50% EUDRAGIT RL, 50% EUDRAGIT RS; and 10% EUDRAGIT RL, 90% Eudragit RS (each commercially available from Rohm Pharma GmbH, Weiterstat, Germany).

The sustained-release coating can also comprise a mixture of a hydrophobic material and a hydrophilic material. The ratio of hydrophobic material to hydrophilic material is determined by, among other factors, the required release rate of the therapeutic agent and the solubility characteristics of the materials selected. Hydrophilic materials include, but are not limited to, polyvinylpyrrolidone and water soluble celluloses, such as hydroxypropylmethyl cellulose. Examples of combinations of hydrophobic material and hydrophilic material useful for the sustained-release coating include, but are not limited, to a combination of shellac and polyvinylpyrrolidone and a combination of ethyl cellulose and hydroxypropylmethyl cellulose.

Alternatively, the therapeutic agent can be dispersed in a controlled-release matrix. The phrase "controlled-release matrix," as used herein means a matrix that slowly releases the therapeutic agent over time. Any controlled-release matrix can be used in the oral dosage form of the invention. Certain controlled-release matrices are known for oral formulations (See, e.g., Remingtons Pharmaceutical Sciences, 18$^{th}$ ed. Mack Publishing Co., Easton, Pa., 1990, p. 1684-1685). Other examples of useful controlled-release matrices are described in U.S. Pat. Nos. 6,143,328 to Heafield et al.; U.S. Pat. No. 6,063,405 to Drizen et al.; U.S. Pat. No. 5,462,747 to Radebaugh et al.; U.S. Pat. No. 5,451,409 to Rencher et al.; U.S. Pat. No. 5,334,392 to Cuine et al.; and 5,266,331, 5,549,912, 5,508,042, 5,656,295, 5,324,351, 5,356,467, and 5,472,712, each to Oshlack et al., the contents of which are expressly incorporated herein by reference thereto. Particularly useful controlled-release matrices for opioids are described in U.S. Pat. No. 6,143,328 to Heafield et al. and U.S. Pat. Nos. 5,266,331, 5,549,912, 5,508,042, 5,656,295, 5,324,351, 5,356,467, and 5,472,712, each to Oshlack et al.

The controlled-release matrix can be a fusible hydrophobic material, optionally combined with a hydrophilic material. The hydrophobic fusible material can be, for example, a hydrophobic polymer or a natural or synthetic wax or oil, such as hydrogenated vegetable oil or hydrogenated castor oil, which in one embodiment has a melting point of from about 35 to 100° C., and in another embodiment from about 45 to 90° C. The hydrophilic material can be a hydrophilic polymer; a water soluble fusible material, such as polyethylene glycol; or a water soluble particulate material, such as dicalcium phosphate or lactose.

The therapeutic agent dispersed in a controlled-release matrix can be prepared by formulating, e.g., using dry or wet granulation or by blending, the therapeutic agent with a component other than the fusible component. Suitable nonfusible materials for inclusion in a controlled release matrix include, but are not limited to:

(a) hydrophilic or hydrophobic polymers, such as gums, cellulose ethers, protein-derived materials, nylon, acrylic resins, polylactic acid, polyvinylchloride, starches, polyvinylpyrrolidones, and cellulose acetate phthalate. Of these polymers, cellulose ethers, for example substituted cellulose ethers such as alkylcelluloses (e.g., ethylcellulose), $C_1$-$C_6$ hydroxyalkylcelluloses (e.g., hydroxypropylcellulose and hydroxyethyl cellulose), and acrylic resins (e.g., methacrylates such as methacrylic acid copolymers) are used in one embodiment. The controlled-release matrix can conveniently contain between 1% and 80% (by weight) of the hydrophobic and/or hydrophilic polymer.

(b) digestible, long chain ($C_8$-$C_{50}$, in one embodiment $C_8$-$C_{40}$) substituted or unsubstituted hydrocarbons, such as fatty acids; hydrogenated vegetable oils; fatty alcohols, such as lauryl, myristyl, stearyl, cetyl or, in one embodiment cetostearyl alcohol; glyceryl esters of fatty acids, for example, glyceryl monostearate; mineral oils; and waxes, such as beeswax, glycowax, castor wax, and carnauba wax. Hydrocarbons having a melting point of between about 25° C. and 90° C. are used in one embodiment. Of these long chain hydrocarbon materials, fatty (aliphatic) alcohols are useful in one embodiment. The controlled-release matrix may contain up to 60% (by weight) of at least one digestible, long chain hydrocarbon.

(c) Polyalkylene glycols. The controlled-release matrix may contain up to 60% (by weight) of at least one polyalkylene glycol.

A suitable controlled-release matrix for use in the oral dosage form of the invention comprises one or more cellulose ethers or acrylic resins, one or more $C_{12}$-$C_{36}$, in one embodiment $C_{12}$-$C_{22}$, aliphatic alcohols, and/or one or more hydrogenated vegetable oils. A particular suitable matrix comprises one or more alkylcelluloses, one or more $C_{12}$-$C_{36}$, in one embodiment $C_{12}$-$C_{22}$, aliphatic alcohols, and optionally one or more polyalkylene glycols. In another embodiment the matrix contains between about 0.5% and 60%, and in another embodiment, between 1% and 50% (by weight) of the cellulose ether.

The acrylic resin is for example a methacrylate such as methacrylic acid copolymer USNF Type A (EUDRAGIT L), Type B (EUDRAGIT S,), Type C (EUDRAGIT L 100-55), EUDRAGIT NE 30 D, EUDRAGIT E, EUDRAGIT RL, or EUDRAGIT RS (commercially available from Rohm Pharma GmbH, Weiterstat, Germany). In one embodiment the matrix contains between about 0.5% and 60% by weight, and in another embodiment between 1% and 50% by weight of the acrylic resin.

In the absence of polyalkylene glycol, the matrix in one embodiment contains between about 1% and 40%, in another embodiment between about 2% and 36% (by weight) of the aliphatic alcohol. When polyalkylene glycol is present in the oral dosage form, then the combined weight of the aliphatic alcohol and the polyalkylene glycol in one embodiment constitutes between about 2% and 40%, in another embodiment between about 2 and 36% (by weight) of the matrix.

The polyalkylene glycol may be, for example, polypropylene glycol or, in one embodiment, polyethylene glycol. The number average molecular weight of the at least one polyalkylene glycol is in one embodiment between 200 and 15,000, and in another embodiment between 400 and 12,000.

The controlled-release matrix containing the therapeutic agent can readily be prepared by dispersing the therapeutic agent in the components of the matrix using conventional pharmaceutical techniques including, but not limited to, melt granulation, wet granulation, dry blending, dry granulation, and co-precipitation.

The controlled-release formulations slowly release the therapeutic agent when ingested and exposed to gastric and/or intestinal fluids.

5.4.5 Coating Process

In one embodiment the first and second compositions are solids, such as, but not limited to, granules, fine granules, pills, beads, capsules, tablets, or powders. Methods for preparing these solids are well known in the art. The compositions can additionally comprise any conventional pharmaceutically acceptable excipient such as a binding agent (e.g., pregelatinised maize starch, polyvinylpyrrolidone or hydroxypropyl methylcellulose); filler (e.g., lactose, microcrystalline cellulose or calcium hydrogen phosphate); lubricant (e.g., magnesium stearate, talc or silica); disintegrant (e.g., potato starch or sodium starch glycolate); or wetting agent (e.g., sodium lauryl sulphate). Such compositions, if desired, can also contain a minor amount of an emulsifying agent or a pH-buffering agent. In one embodiment, the first and/or second composition comprises a hydrophobic material to provide the composition with a sustained-release property. Examples of useful hydrophobic material are disclosed in section 5.4.4, supra. Solid compositions can be prepared by using conventional methods known in the art, for example, wet granulation, melt extrusion, and tableting by compression.

The solid compositions are coated with layers by applying one or more coating mixtures. Coating mixtures are prepared by any conventional means, for example, by dissolving the above-mentioned polymers and optionally plasticizers in a suitable solvent or mixture of solvents, for example water, methanol, ethanol, isopropanol, acetone, ethylacetate, ethylene chloride, or mixtures thereof. Examples of plasticizers include, but are not limited to, citric acid esters, such as triethyl citrate and tributyl citrate; dibutyl phthalate; 1,2-propylene glycol; polyethylene glycols; castor oil; and triacetin. If the coating mixture is an aqueous dispersion, a small amount of talc, glyceral monostearate, or colloidal silicon dixide may be added to reduce the tendency of the aqueous dispersion to stick during processing. The coating mixture can also contain additives such as coloring agents and/or magnesium stearate, which are well known in the coating art.

The coating solution can be applied to the solid composition by any means available to those of ordinary skill in the art such as, for example, spraying or dipping. Conventional coating apparatuses, well known to those of ordinary skill in the art, can be used to coat the solid composition (See, e.g., Remingtons Pharmaceutical Sciences, 18th ed. Mack Publishing Co., Easton, Pa., 1990). Conventional coating apparatuses include, but are not limited to, coating-granulating apparatuses of the centrifugal fluidized type, pan-coating apparatuses, and fluidized-bed granulating coating apparatuses. For example, a Wuster fluidized-bed system can be used in which an air jet, injected from underneath, fluidizes the coated material and effects drying while the polymer coating is sprayed on. When the solid composition is coated with more than one coating, the first coating solution is applied and then allowed to dry before the second coating solution is applied. In one embodiment, the coating solutions are applied to provide a dosage form that has a dissolution profile substantially unaffected by exposure to accelerated-storage conditions.

The phrase "accelerated-storage conditions," as used herein, means storage conditions of elevated temperature and/or elevated relative humidity to which the oral dosage form is subjected for the purpose of obtaining regulatory approval, e.g., the FDA for approval in the U.S., and an expiration date. For example, a generally accepted test employed in FDA guidelines relates to the storage of a drug product (i.e., in its container and package) at 40° C. and 75% Relative Humidity (RH). The length of time that the drug product can be stored under these conditions without chemically degrading and with its dissolution and physical characteristics remaining unchanged, is used to determine the expiration date of the drug product. For example, storage for three months without chemical degradation and without change in dissolution or appearance can result in the drug product being accorded a two year expiration date. Other generally accepted accelerated tests include those where the drug product is subjected to storage at 37° C. and 80% relative humidity for one month or longer, in one embodiment three months.

5.5 Oral Dosage Form 5.5.1 Amount Per Dosage Unit

In the oral dosage form of the present invention, the amount of the therapeutic agent per dosage unit is that which is an effective amount for its particular indication and is independent of the amount of the adverse-effect agent. For example, if the therapeutic agent is an opioid agonist, the amount of the opioid agonist in the oral dosage form of the present invention is generally from about 75 ng to about 1000 mg, in one embodiment from about 75 ng to about 750 mg. One of ordinary skill in the art can readily determine, without undue experimentation, the amount of therapeutic agent needed for a particular indication.

The amount of the adverse-effect agent in the oral dosage form of the present invention is such that the adverse-effect agent can give the intended adverse effect. When the adverse-effect agent is intended to reduce or eliminate the pharmacological effects of the therapeutic agent, the amount of the adverse-effect agent in the oral dosage form is at least sufficient to reduce or eliminate the effects of the therapeutic agent when both agents are released.

In the present invention, the phrase "to reduce or eliminate the effects of the therapeutic agent," as used herein, means that the effects of the therapeutic agent that attract potential abusers are eliminated or become lessened. For example, an adverse-effect agent can reduce the euphoric effect of a therapeutic agent.

When the adverse-effect agent is an opioid antgonist, the amount of the opioid antagonist, present in a oral dosage form of the present invention, can be from about 10 ng to 275 mg. The opioid antagonists cyclazocine and naltrexone, when administered orally, retain much of their efficacy with a long duration of action, approaching 24 hours, Accordingly, amounts of less than 100 mg of these opioid antagonists are typically used in the oral formulations of the invention.

When the adverse-effect agent is intended to cause an undesired physiological reaction, such as a emesis, the amount of the adverse-effect agent in the oral dosage form is at least sufficient to cause such effect upon release.

For safety reasons, the amount of the adverse-effect agent present in the oral dosage form should not be harmful to humans even if fully released. One of ordinary skill in the art can readily determine, without undue experimentation, the amount of adverse-effect agent needed to elicit the intended adverse-effect without being harmful.

In certain embodiments of the present invention, the ratio of the therapeutic agent to the adverse-effect agent in the oral dosage form is about 1:1 to about 50:1 by weight, in one embodiment about 1:1 to about 20:1 by weight. In certain other embodiments, the ratio is about 1:1 to about 10:1 by weight. In another embodiment of the invention, the therapeutic agent includes oxycodone or hydrocodone and is present in the amount of about 15-45 mg, and the adverse-effect agent includes naltrexone and is present in about 0.5-5 mg.

In another embodiment the first composition has a sustained-release coating, the therapeutic agent is an opioid agonist and the adverse-effect agent is an opioid antagonist. In embodiments in which the opioid agonist is hydrocodone, the sustained-release oral dosage forms can include analgesic doses from about 5 mg to about 80 mg of hydrocodone per dosage unit. In oral dosage forms where the opioid agonist is hydromorphone, it may be included in an amount from about 2 mg to about 64 mg hydromorphone hydrochloride per dosage unit. In another embodiment, the opioid agonist is morphine, and the oral dosage forms of the present invention include from about 2.5 mg to about 800 mg morphine per dosage unit. In yet another embodiment, the opioid agonist is oxycodone and the oral dosage forms include from about 2.5 mg to about 800 mg oxycodone, in another embodiment from about 20 mg to about 30 mg oxycodone per dosage unit. Controlled-release oxycodone formulations are known in the art. The opioid agonist can be tramadol in an amount from about 25 mg to 800 mg tramadol per dosage unit. The dosage form can contain more than one opioid agonist.

5.5.2 Embodiments of the Oral Dosage Form

In one embodiment, the first composition and the second composition are coated as explained in section 5.4, supra to provide the first coated composition and the second coated composition. As discussed above, the first composition, comprising a therapeutic agent, is coated with an outer acid-soluble layer, an inner base-soluble layer and, optionally, an innermost sustained release coating; and the second composition, comprising an adverse-effect agent, is coated with an inner acid-soluble layer, an outer base-soluble layer, and, optionally, a layer substantially insoluble in the gastrointestinal tract. The first composition and the second composition are then combined to provide a unit dosage of the oral composition of the invention. In one embodiment, the first composition and the second composition are similar in their size, shape and color so that they cannot be readily distinguished from each other. For example, the first composition and the second composition can each be powders, granules, or beads that are combined and incorporated into a capsule or tablet using methods well known to those of ordinary skill in the art. The capsule may be hard or soft, for example, gelatin. The capsule can also contain pharmaceutically acceptable excipients.

Figure 3:
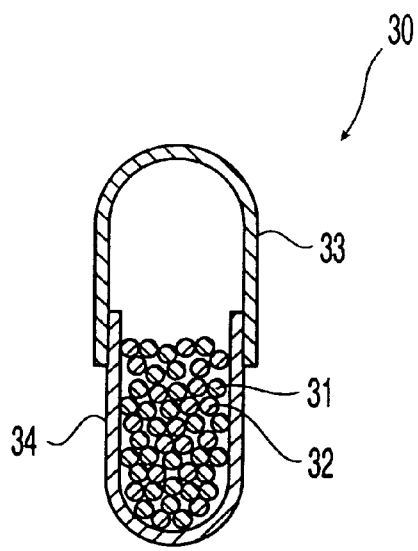
FIG. 3 shows a cross-sectional view of a first embodiment of the invention, which is a capsule containing coated granules of a first composition and coated granules of a second composition.

FIG. 3 shows a cross-sectional view of a capsule 30, which has a first part 33 and a second part 34 and contains powders, granules, or beads of a first composition 31 and powders or granules of a second composition 32.

Figure 5:
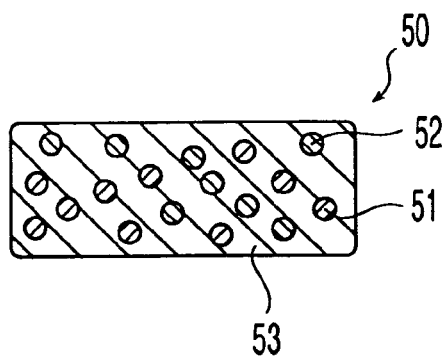
FIG. 5 shows a cross-sectional view of a third embodiment of the invention, which is a tablet containing coated granules of a first composition and coated granules of a second composition.

FIG. 5 shows a cross-sectional view of a dosage form according to the invention in the form of a tablet 50. The first composition is in the form of powders or granules 51 and the coated second composition is in the form of powders, granules, or beads 52. The first composition and the coated second composition are mixed with a pharmaceutically acceptable matrix 53 and compressed into a tablet.

In another embodiment the capsule or tablet contains the first composition without the outer acid-soluble layer and without the inner base-soluble layer and the second composition coated with an outer base-soluble layer and an inner acid-soluble layer.

Figure 6:
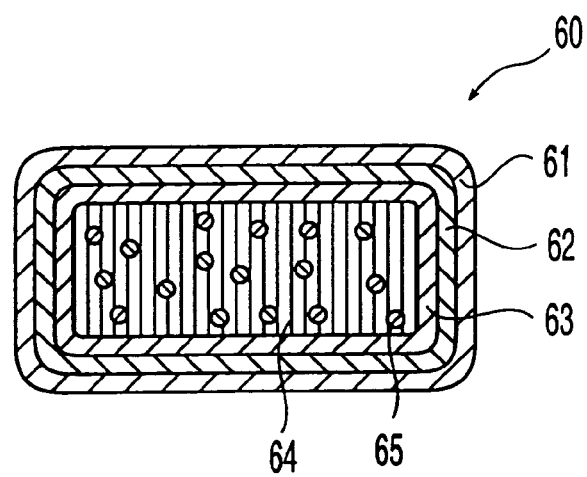
FIG. 6 shows a cross-sectional view of a fourth embodiment of the invention, which is a coated tablet containing a first composition, with granules of a coated second composition dispersed throughout the first composition.

FIG. 6. Depicts another embodiment of the oral dosage form of the invention in the form of a tablet comprising a core that is a mixture of an uncoated first composition 64 and a second composition coated with a base-soluble outer layer and an acid soluble inner layer 65. The core is then coated with an inner base-soluble layer 62, and an outer acid-soluble layer 61, and an optional innermost sustained release coating 63. Alternatively, the second composition can be coated with a layer that is substantially insoluble in the gastrointestinal tract.

Figure 4:
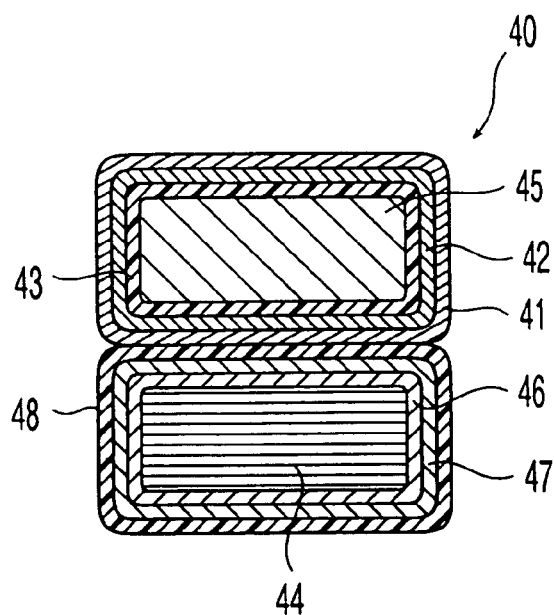
FIG. 4 shows a cross-sectional view of a second embodiment of the invention, which is a two-layer tablet.

Another embodiment of the oral dosage form of the invention is a two-layer tablet 40 as shown in FIG. 4. A solid nucleus of the first composition 45 is covered with an innermost sustained-release coating 43 (optional), an inner base-soluble layer 42, and an outer acid-soluble layer 41. A solid nucleus of the second composition 44 is covered with an inner acid-soluble layer 46, an outer base-soluble layer 47, and an outermost layer that is substantially insoluble in the gastrointestinal tract 48 (optional). The two coated nuclei are then compressed into a two-layer tablet 40 using conventional tableting equipment and standard techniques to provide a two-layered tablet. The compressed two-layer tablet can then optionally be coated with an additional coating to provide a tablet of uniform appearance. In one embodiment, the additional coating is a coating that dissolves in the stomach after the tablet is swallowed.

In another embodiment of the two-layer tablet, the first composition is uncoated, i.e., is not covered with the outer acid-soluble layer or the inner base-soluble layer, but the second composition is coated with an outer base-soluble layer and an inner acid-soluble layer.

Figure 7:
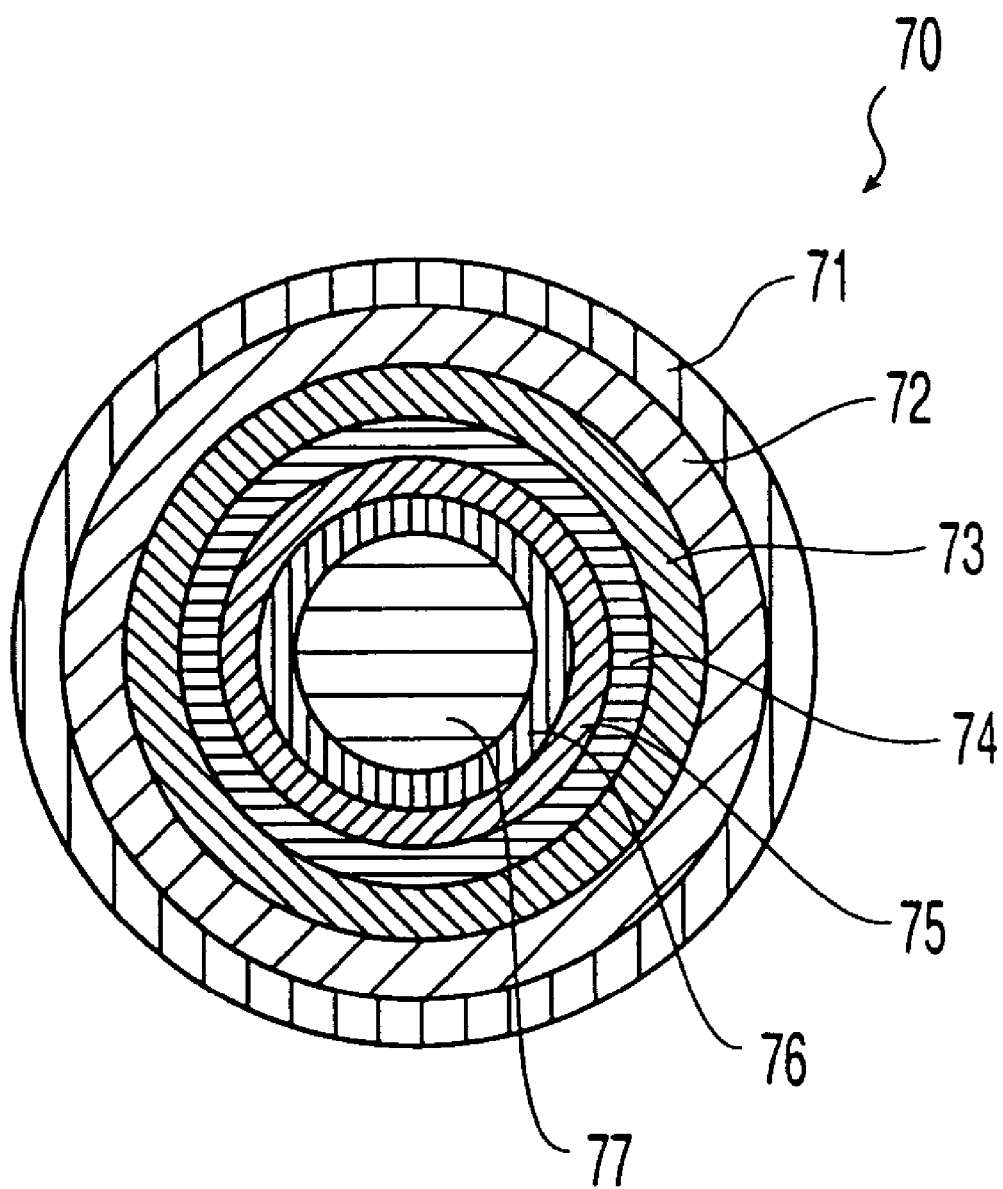
FIG. 7 shows a cross-sectional view of a fifth embodiment of the invention, which is a tablet wherein a coated composition of the adverse-effect agent is further coated with the therapeutic agent and then the therapeutic agent is coated.

Yet another embodiment of the oral dosage 70 is shown in FIG. 7. A solid nucleus of the second composition 77 is coated with an innermost acid-soluble layer 76 and an outer base-soluble layer 75. Then, the second composition is further coated with a layer of the first composition 74, an optional innermost pH-independent layer 73, an inner base-soluble layer 72, and an outer acid-soluble layer 71. The oral dosage 70 may be a tablet or a granule.

6. EXAMPLES

The following prophetic examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

Capsule (1) Preparation of Oxycodone Granules and Naltrexone HCl Granules

| Ingredient | Amount/unit (mg) |
| --- | --- |
| Oxycodone HCl or | 20.00 |
| Naltrexone HCl | 5.00 |
| Spray Dried Lactose | 59.25 |
| Providone | 5.00 |

-continued

| Ingredient | Amount/unit (mg) |
| --- | --- |
| Eudragit RS 30D (dry wt.) | 10.00 |
| Triacetin | 2.00 |
| Total | 131.00 |

EUDRAGIT RS 30 D is plasticized by mixing with triacetin. The dispersion is then combined with the oxycodone HCl or naltrexene HCl, spray dried lactose, and providone using a fluid-bed granulator. The resulting mixture is granulated. If necessary the granules are dried. The granules are then screened with a sieve to provide granules of an appropriate size.

(2) Coating

An acid-soluble coating solution is prepared by dispersing 15.0 g EUDRAGIT E100 in 200 ml of ethanol to provide a clear solution, and 4 g of the plasticizer triethyl citrate is added to the solution.

A base-soluble coating solution is prepared by dispersing 15.0 g EUDRAGIT L in 200 ml of ethanol to provide a clear solution.

The oxycodone HCl granules are spray coated with the base-soluble coating solution and dried. After drying, the resulting oxycodone HCl granules coated with the base-soluble coating are then spray coated with the acid-soluble coating solution and the resulting granules dried.

The naltrexone HCl granules are spray coated with the acid-soluble coating solution and dried. After drying, the resulting naltrexone HCl granules coated with the acid-soluble coating are then spray coated with the base-soluble coating solution and the resulting granules dried.

(3) Encapsulating

The coated oxycodone HCl granules and the coated naltrexone HCl granules are mixed together to provide a mixture, and a gelatin capsule is filled with the mixture.

Example 2

Tablet

Stearyl alcohol is melted, and the melted stearyl alcohol (25.00 mg per unit) is mixed with the coated granules obtained in Example 1 to wax them. The waxed granules are cooled in a fluid bed dryer and then blended with talc (2.50 mg per unit) and magnesium stearate (1.25 mg per unit) to provide a blend. The resulting blend is compressed into a tablet using a tablet press.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference.

What is claimed is:

1. An oral dosage form comprising a first composition and a second composition, wherein the first composition comprises an effective amount of a therapeutic agent and is coated with an inner base-soluble layer and an outer acid-soluble layer and the second composition comprises an effective amount of an adverse-effect agent and is coated with an inner acid-soluble layer and an outer base-soluble layer.

2. The oral dosage form of claim 1, wherein the first composition and the second composition are in the form of powders, granules, or beads contained within a capsule.

3. The oral dosage form of claim 1, wherein the first composition and the second composition are in the form of granules or a powder dispersed in a pharmaceutically acceptable matrix.

4. The oral dosage form of claim 1 in the form of a two-layer tablet having a first layer comprising the first composition and a second layer comprising the second composition.

5. The oral dosage form of claim 4, wherein the two-layer tablet is further coated with a coating that dissolves in the stomach.

6. The oral dosage form of claim 1 in the form of a tablet comprising a core coated with an inner-base soluble layer and an outer acid soluble layer, wherein the core comprises the second composition coated with an inner acid-soluble layer and an outer base-soluble layer dispersed within the therapeutic agent.

7. The oral dosage form of claim 1 in the form of a tablet comprising a core of the second composition coated with an inner acid-soluble layer, an outer base-soluble layer, a coating of the first composition, an inner-base-soluble layer, and an outer acid-soluble layer.

8. The oral dosage form of claim 1, wherein the adverse-effect agent is an antagonist of the therapeutic agent.

9. The oral dosage form of claim 1, wherein the adverse-effect agent is laxative.

10. The oral dosage form of claim 1, wherein each acid-soluble layer is soluble at a pH value of less than about 5.0 and substantially insoluble at a pH value of greater than about 5.5.

11. The oral dosage form of claim 1, wherein each base-soluble layer is soluble at a pH value of greater than about 5.5 but substantially insoluble at a pH value of less than about 5.0.

12. The oral dosage form of claim 1, wherein each acid-soluble layer comprises a cationic polymer with dimethylaminoethyl ammonium functionalities.

13. The oral dosage form of claim 1, wherein each base-soluble layer comprises an anionic polymer of methacrylic acid or a methacrylate with carboxylic acid functionalities.

14. The oral dosage form of claim 1, wherein the first composition is a controlled-release dosage form.

15. The oral dosage form of claim 14, wherein the first composition is coated with an inner-most sustained-release coating.

16. The oral dosage form of claim 15, wherein the sustained-release coating is selected from the group consisting of a wax, fatty alcohol, shellac, zein, hydrogenated vegetable oil, water insoluble cellulose, polymers of acrylic acid, polymers of methacrylic acid, copolymers of acrylic acid and methacrylic acid, and mixtures thereof.

17. The oral dosage form of claim 14, wherein the first composition is dispersed in a controlled-release matrix.

18. The oral dosage form of claim 1, wherein the therapeutic agent is selected from a group consisting of analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

19. The oral dosage form of claim 1, wherein the therapeutic agent is an agent having a potential for abuse.

20. The oral dosage form of claim 19, wherein the therapeutic agent is an opioid, benzodiazepine, barbiturate, or a stimulant.

21. The oral dosage form of claim 20, wherein the therapeutic agent is an opioid and the adverse-effect agent is an opioid antagonist.

22. The oral dosage form of claim 21, wherein the opioid is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures thereof.

23. The oral dosage form of claim 22, wherein the opioid selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol, pharmaceutically acceptable salts thereof, and mixtures thereof.

24. The oral dosage form of claim 23, wherein the opioid is oxycodone or hydrocodone.

25. The oral dosage form of claim 21, wherein the adverse-effect agent is selected from the group consisting of naloxone, naltrexone, nalmefene, cyclazacine, and levallorphan.

26. The oral dosage form of claim 21, wherein the adverse-effect agent is naloxone or naltrexone.

27. The oral dosage form of claim 20, wherein the therapeutic agent is a benzodiazepine and the adverse-effect agent is a benzodiazepine antagonist.

28. The oral dosage form of claim 27, wherein the benzodiazepine is selected from the group consisting of alprazolam, bromazepam, chlordiazepoxied, clorazepate, diazepam, estazolam, flurazepan, halazepam, ketazolam, lorazepam, nitrazepam, oxazepam, prazepam, quazepam, temazepam, triazolam, pharmaceutically acceptable salts thereof, and mixtures thereof.

29. The oral dosage form of claim 27, wherein the benzodiazepine antagonist is flumazenil.

30. The oral dosage form of claim 20, wherein the therapeutic agent is a barbiturate and the adverse-effect agent is a barbiturate antagonist.

31. The oral dosage form of claim 30, wherein the barbiturate is selected from the group consisting of amobarbital, aprobarbotal, butabarbital, butalbital, methohexital, mephobarbital, metharbital, pentobarbital, phenobarbital, secobarbital, pharmaceutically acceptable salts thereof, and mixture thereof.

32. The oral dosage form of claim 20, wherein the barbiturate antagonist is a stimulant.

33. The oral dosage form of claim 20, wherein the therapeutic agent is a stimulant and the adverse-effect agent is a stimulant antagonist.

34. The oral dosage form of claim 33, wherein the amphetamine is selected from the group consisting of amphetamine, amphetamine and dextroamphetamine resin complex, dextroamphetamine, methamphetamine, methylphenidate, a pharmaceutically acceptable salt thereof, and mixtures thereof.

35. The oral dosage form of claim 33, wherein the stimulant antagonist is a benzodiazepine.

36. The oral dosage form of claim 20, wherein the therapeutic agent is selected from a group consisting of dronabinol, glutethimide, methylphenidate, nabilone, anabolic steroids, methylprylon, ethchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, detropropoxyphene, pharmaceutically acceptable salts thereof, and mixtures thereof.

37. The oral dosage form of claim 1, wherein the therapeutic agent is selected from the group consisting of 5-ASA, steroids, laxatives, octreotide, cisapride, anticholinergics, calcium channel blockers, DNA for delivery to the cells of the colon, glucosamine, thromboxane $A_2$ synthetase inhibitor, 5HT3-antagonists, antibodies against infectious bacteria, antiviral agents, heparins, insulin, calcitonins, human growth hormone, growth hormone releasing hormon, interferons, somatostatin and analogues thereof, erythropoietin, granulocyte colony stimulating factor, parathyroid hormone, luteinising hormone releasing hormone and analogues thereof, atrial natriuretic factor, vasopressin, desmopressin, calcitonin gene related peptide, and analgesics.

38. The oral dosage form of claim 1, wherein the ratio of therapeutic agent to adverse-effect agent is from about 1:1 to 50:1.

39. A method for treating pain, comprising administering to a patient in need thereof the oral dosage form of claim 1.

* * * * *